(12) United States Patent
Dugas et al.

(10) Patent No.: US 6,426,068 B1
(45) Date of Patent: Jul. 30, 2002

(54) THERAPEUTIC USES OF HETEROLOGOUS SUPEROXIDE DISMUTASE (HSD), AND METHOD FOR SELECTING SAID HSD

(75) Inventors: Bernard Dugas, Verrieres le Buisson; Alphonse Calenda, Boulogne; Jacques Sauzieres, Saint-Remy-les-Chevreuse; Eric Postaire, Vanves, all of (FR)

(73) Assignee: Fractales Biotech, Paris (FR)

( * ) Notice: Subject to any disclaimer, the term of this patent is extended or adjusted under 35 U.S.C. 154(b) by 0 days.

(21) Appl. No.: 09/600,062

(22) PCT Filed: Jan. 12, 1999

(86) PCT No.: PCT/FR99/00031

§ 371 (c)(1),
(2), (4) Date: Sep. 6, 2000

(87) PCT Pub. No.: WO99/35247

PCT Pub. Date: Jul. 15, 1999

(30) Foreign Application Priority Data

Jan. 12, 1998 (FR) .............................................. 98 00205

(51) Int. Cl.[7] ........................ C12N 9/02; G01N 33/567; C12Q 1/26; A61K 38/44; A61K 38/00
(52) U.S. Cl. ..................... 424/94.1; 435/189; 435/7.21; 435/25; 514/12
(58) Field of Search ................................ 435/189, 7.21, 435/25; 424/94.4; 514/12

(56) References Cited

U.S. PATENT DOCUMENTS 5,196,335 A * 3/1993 Groner et al. ........... 435/240.2
5,714,362 A * 2/1998 Groner et al. .............. 435/189

OTHER PUBLICATIONS

Wim Van Camp, Chris Bowler, Raimundo Villarroel, Ed W.T. Tsang, Marc Van Montagu, Dirk Inzé ; "Characterization of iron superoxide dismutase cDNAs from plants obtained by genetic complementation in *Escherichia coli*"; *Proceedings of the National Academy of Sciences of the United States of America*; Dec. 1990; pp. 9903–9907; vol. 87; Journal Code: PV3, ISSN: 0027–8424; XP002081154 United States.

Michael Westendorp, Vladimir A. Shatrov, Klaus Schulze–Osthoff, Ranier Frank, Margot Kraft, Marek Los, Peter H. Krammer, Wulf Dröge, Volker Lehmann; "HIV–I Tat potentiates TNF–induced NF–Kappab activation and cytotoxicity by altering the cellular redox state"; *EMBO Journal*; 1995; pp. 546–554; vol. 14, No. 3; XP002081155.

L.A. MacMillian–Crow, John P. Crow, Jeffrey D. Kerby, Joseph S. Beckman, John A. Thompson; "Nitration and inactivation of manganese superoxide dismutase in chronic rejection of human renal allografts"; *Proceedings of the National Academy of Sciences, USA*; Oct. 1996; pp. 11853–11858; vol. 93; XP002081156.

* cited by examiner

Primary Examiner—Rebecca E. Prouty
Assistant Examiner—Malgorzata Walicka
(74) Attorney, Agent, or Firm—Alston & Bird LLP

(57) ABSTRACT

The invention concerns novel therapeutic uses of heterologous superoxide dismutase (HSD) for preparing medicines for treating diseases in which cell and organic degeneration is observed, and a method for selecting said HSD.

8 Claims, 20 Drawing Sheets

THERAPEUTIC USES OF HETEROLOGOUS SUPEROXIDE DISMUTASE (HSD), AND METHOD FOR SELECTING SAID HSD

FIELD OF THE INVENTION

The present invention relates to the demonstration of immuno-redox activities of heterologous SODs (HSDs) and to a novel therapeutic use, as well as to a method for selecting said HSDs.

BACKGROUND OF THE INVENTION

Under the normal conditions of oxygen pressure, oxygen gives rise to reactive oxygen (hydrogen peroxide and free radicals such as superoxide anions, hydroxyl radicals or nitric oxide), which is rapidly destroyed by cells which have at least three major endogenous mechanisms for autoregulation of the reactive oxygen produced (antioxidant substances, metal chelators, detoxifying enzymes).

Conversely, if these mechanisms are affected, or if the production of reactive oxygen, and in particular free radicals, is too great, an oxidative stress and the appearance of a pathological state results therefrom.

Superoxide dismutases or SODs, which form a class of metalloproteins containing iron, copper, zinc or manganese, are enzymes which are capable of inducing the dismutation of superoxide anions to protect cells against the toxicity of these superoxide radicals ($O_2^-$).

Superoxide anions generally form when molecular oxygen acquires an additional electron, which happens when oxygen is subjected to ionizing radiation. This anion has a short life, and is converted into hydrogen peroxide by SOD (dismutation). This dismutation generates hydrogen peroxide which is also a cellular oxidant. To respond to the rise in hydrogen peroxide concentrations, cells increase the activity of enzymes involved in eliminating hydrogen peroxide, i.e. catalase and glutathione peroxidase, in accordance with the following scheme:

In the absence of sufficient amounts of catalase and of glutathione peroxidase, and in the presence of small amounts of iron, which result in particular from cellular lesions, a conversion is obtained of hydrogen peroxide into an even more toxic compound, hydroxyl radicals (Fenton reaction), in accordance with the following scheme:

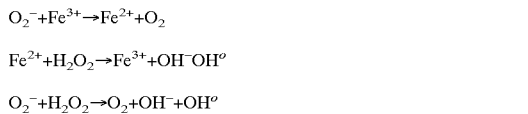

Since oxygen-derived free radicals appear to be involved in many disorders, the use of SOD in therapeutics has thus been advocated in pathologies induced by reactive oxygen such as inflammatory states (inflammatory arthropathies, for example) (R. NORDMANN et al., Cah. Nutr. Diet., 1991, 26, 6, 398–402); in lung diseases, and more particularly broncho-pulmonary dysplasia, or in other toxic conditions linked to the presence of oxygen in considerable amounts (central nervous system, ischaemia, nonvascular gastrointestinal disorders, ocular disorders (locally in the anterior chamber of the eye) or combating the undesirable effects of anti-cancer treatments) SOD has also been proposed, with a greater or lesser degree of success (Greenwald R. A., Free Radical Biol. Med., 1990, 8, 201–209).

Three distinct types of SOD have been described, which fall within two distinct developing families;
- SOD containing copper and zinc, which is usually located in the cytosol of eukaryotic cells, in the extracellular fluid of mammals and in some bacteria;
- SOD containing manganese (MnSOD) or iron (FeSOD), which is usually located in prokaryotes or in mitochondria (MnSOD);
- SOD containing iron (FeSOD), which is located in anaerobic bacteria and prokaryotes.

Among the SODs tested, it is those which exhibit a sustained half-life and a low incidence of accidents of immunological nature which have preference; mention may be made in particular of Cu/Zn—SOD of bovine origin (homodimer which catalyses the dismutation of the superoxide radical), Mn—SOD of *E. coli*, Fe—SOD, liposomal SODs, polyethylene glycol-conjugated SODs, SOD polymers or copolymers, recombinant human CuZn—SOD and Mn—SOD, as well as SODs of plant origin.

SUMMARY OF THE INVENTION

In various inflammation inhibition tests, heterologous SODs are found to exhibit significantly greater anti-inflammatory activity than homologous SODs.

For example:
- in a rat model in which an inflammation is induced with carrageenans, the anti-inflammatory activity of various SODs is as follows: Mn—SOD of *E. coli*>bovine Cu—SOD>human Cu—SOD>yeast Cu—SOD>plant Cu—SOD; in this case, rat Cu—SOD exhibits significant pro-inflammatory activity;
- in a rat model in which an inflammation is induced with adriamycin, the anti-inflammatory activity of various SODs is as follows: bovine Cu—SOD>Mn—SOD of *E. coli*; rat homologous Cu—SOD is totally inactive, whereas yeast Cu—SOD generates a pro-inflammatory response.

The applicant has found, unexpectedly, that, besides a dismutase activity, heterologous SODs (HSDs) possess an immuno-redox activity which it is possible to dissociate from the dismutase activity.

For the purposes of the present invention, "immuno-redox activity" is intended to mean a stimulation of the production of endogenous SOD, catalase and glutathione peroxidase.

Besides the fact that such heterologous SODs with essentially immuno-redox activity do not induce a pro-inflammatory reaction, they induce the production of endogenous SOD and stimulate the production of catalase and of glutathione peroxidase. Such SODs thus increase nonspecific defences which protect against cell and organ degeneration.

A subject of the present invention is the use of a plant heterologous SOD with essentially immuno-redox activity for preparing a medicinal product intended for treating diseases in which cell and organ degeneration is observed.

Such heterologous SODs which increase nonspecific defences protect cells from degeneration; they thus constitute an antidegeneration medicinal product of choice, whatever the origin of the degeneration: degenerative pathology such as radiation-induced aftereffects, Parkinson's disease, Alzheimer's disease, etc., degeneration induced by an infectious agent (AIDS, bilharzia, post-infectious cirrhosis (hepatitis C)) or iatrogenic degeneration (medicinal detoxification action).

According to an advantageous embodiment of said use, said SOD with essentially immuno-redox activity is a nitrated SOD; such an SOD has lost its dismutase activity, whereas it conserves its immuno-redox activity.

It has the advantage of avoiding any risk of pro-inflammatory activity linked to the dismutase activity and to the production of an excess of hydrogen peroxide, when the induction of catalase and glutathione peroxidase production is too weak to satisfy the demand.

Surprisingly, SODs according to the invention (HSDs), which no longer, or practically no longer, exhibit dismutase activity, but which have conserved their immuno-redox activity, used as a medicinal product in humans, stimulate the production of endogenous SOD, as well as the production of catalase and of glutathione peroxidase.

According to another advantageous embodiment of said use, said plant heterologous SOD is in particular derived from melon.

According to another advantageous embodiment of said use, said SODs are used for preparing a medicinal product intended for treating degenerative diseases which are selected from the group consisting of neurodegenerative diseases, cirrhosis, lentivirus infections, parasite infections and iatrogenic diseases (medicinal detoxification).

A subject of the present invention is also a method for selecting a plant heterologous SOD with essentially immuno-redox activity, characterized in that it comprises:
  (a) measuring the dismutase activity of an SOD, or of a modified SOD,
  (b) selecting SODs without dismutase activity or having a dismutase activity which is reduced by at least a factor of 10, and
  (c) measuring the immuno-redox activity of the SODs selected in (b) in a cellular system in which expression of endogenous SOD is inhibited.

According to an advantageous embodiment of said method, step (a) for measuring the dismutase activity is carried out by reduction of ferricytochrome c.

According to another advantageous embodiment of said method, the system according to step (c) consists of cells expressing the Tat protein of HIV-1.

BRIEF DESCRIPTION OF THE DRAWINGS

Additionally, the invention comprises other arrangements which will emerge from the description which follows, which refers to examples of use of the method which is the subject of the present invention, as well as to the attached drawings in which.

DETAILED DESCRIPTION OF THE INVENTION

Figure 1:
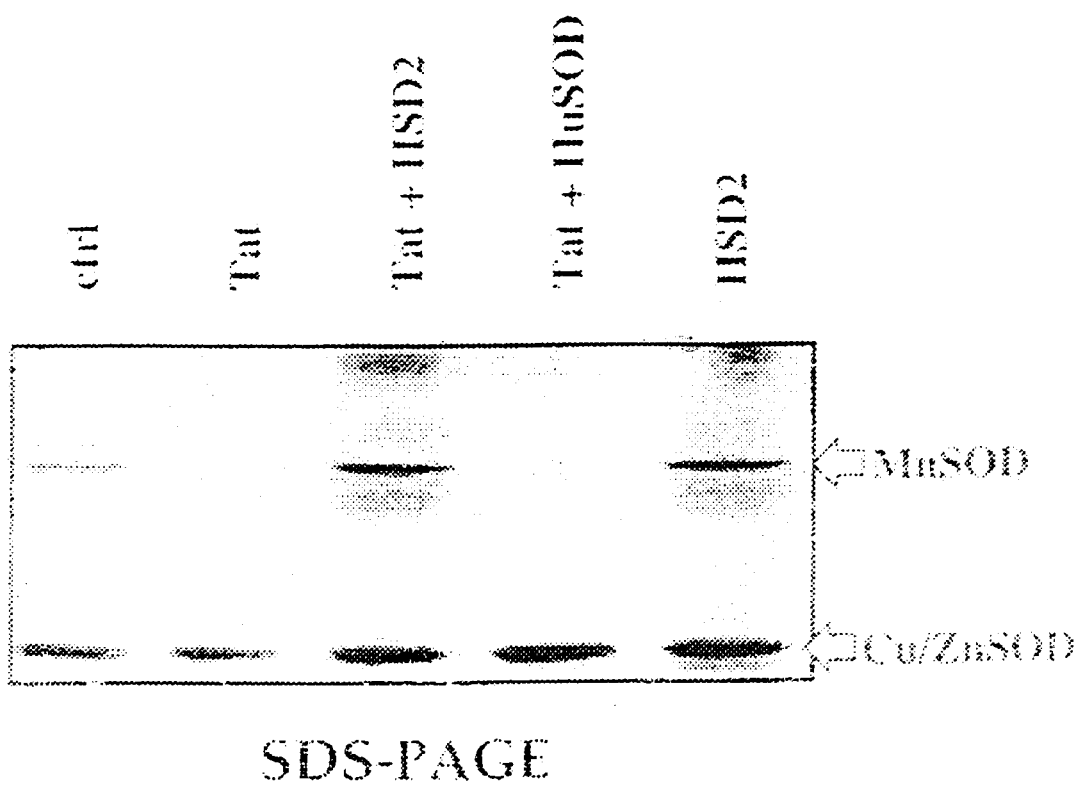
FIG. 1 illustrates the SDS-PAGE electro-phoretic profile of the expression of endogenous SOD in U937 cells under various conditions.

As emerges from the above, the invention is in no way limited to its methods of implementation, preparation and application which have just been described more explicitly; on the contrary, it encompasses all the variants thereof which may occur to persons skilled in the art, without departing from the context or scope of the present invention.

EXAMPLE 1

Demonstration of the Immuno-redox Activity of SODS.

I. Materials and Methods

Cell Culture

The human promonocytic leukaemia cell line U937 is cultured at a final concentration of $2 \times 10^5$ cells/ml in an Iscove medium enriched with 100 U/ml of penicillin, 100 µg/ml of streptomycin and 5% of foetal calf serum, in the presence (activated) or absence (control) of 10 µg/ml of HIV-Tat protein. For each experiment, 30 U/ml of SOD [recombinant human (HuSOD), bovine (HSD1, Sigma, St Louis, Mo.) or plant (derived from melons) (HSD2, Bio-Extraction, Bron, France)] are added to the medium and incubated at 37° C., in a humid atmosphere comprising 5% $CO_2$, for 24 hours.

Determination of Endogenous SOD

U937 cells, untreated or treated with HIV-Tat protein, in the presence or absence of the abovementioned SODs, are lysed in a detergent buffer comprising: 10 mM Tris-HCl pH 7.4, 0.1% of SDS, 1% of Nonidet P-40, 10 µg/ml of leupeptin, 100 µg/ml of PMSF and 2 µg/ml of aprotinin, by heating at 85° C. for 5 min. The lysate is then briefly sonicated (3×30 sec).

20-µg samples are subjected to an electrophoresis under reducing conditions on a 12% SDS-polyacrylamide gel. The proteins are then analysed by electroblotting on a 0.2 µm vinylidene difluoride membrane which is subsequently blocked with 10 mM Tris-HCl, pH 7.4, 100 mM NaCl (TBS) containing 1% of bovine serum albumin (BSA) and 0.1% of Tween 20.

The imprints are then incubated with a rabbit anti-human SOD antiserum or with a rabbit preimmune serum at a final concentration of 2 µg/ml. The imprints are then washed twice with TBS containing 0.1% of Tween 20, then incubated with a horseradish peroxidase-conjugated goat anti-rabbit Ig, and the bands are revealed by chemiluminescence (luminol) and detected by autoradiography (film sensitive to blue light).

Determination of Dismutase Activity of the Endogenous SOD

The total superoxide dismutase activity is measured on the sonicated lysates obtained as described above by its capacity to inhibit the reduction of ferrocytochrome c by the superoxide radicals produced by the xanthin oxidase/xanthine system (McCord. J. M., 1969, J. Biol. Chem. 244, 6049). One unit of superoxide dismutase is defined as the amount which inhibits 50% of the reduction of cytochrome c at room temperature and at pH 7.8.

Determination of Immuno-redox Activity of the Plant Heterologous SOD

After stimulation and treatment with various sources and concentrations of SOD, the U937 cells are harvested in a phosphate-buffered cold physiological saline, and counted. The total RNA is extracted by standard techniques (Chomczynski. P., 1987, Anal. Biochem. 162, 156), in 1 ml of TRIzol reagent (Life Technologies ≠15596), according to the manufacturer's instructions. After its extraction, the RNA is precipitated with isopropyl alcohol, and the pellets are washed in 70% ethanol and air dried. The dried pellets are resuspended in 50 µl of 0.5 mM EDTA, pH 8, and quantified by spectrophotometry.

For the reverse transcription, 2 µg of total RNA in 10 µl are then used to synthesize the cDNA, in the presence of the universal primer oligo-dT [Young R. A., 1983, Proc. Natl. Acad. Sci. USA, 80, 1194] in the following reaction mixture; 1 µl of Superscript II reverse transcriptase [Life Technologies # 18089] with 6 µl of 5×reverse transcription buffer (250 mM Tris-HCl, pH 8.3, at 42° C., 50 mM MgCl$_2$, 300 mM KCl, 50 mM DTT), 0.5 µl of RNAase inhibitor, 1.5 µl of oligo-dT (1 mg/ml) and 6 µl of 2.5 mM dNTP (Boehringer Mannheim).

After a 5-min. incubation of the total RNA at 65° C. and cooling on ice, the reaction mixture is added, and the reaction takes place for one hour at 42° C.

For the PCR amplification, the same amount of cDNA is subjected to thirty cycles in a reaction volume of 50 µl (25 mM TAPS pH 9.3, 50 mM KCl, 1 mM MgCl$_2$, 100 pM of each dNTP, 20 µM of each primer and one unit of Goldstar polymerase).

The amplification program comprises: five cycles comprising 60 sec. at 92° C., 60 sec. at 58° C. and 60 sec. at 74° C., followed by 25 cycles comprising 30 sec. at 92° C., 60 sec. at 60° C. and 60 sec. at 74° C., and to finish, the temperature is kept at 74° C. for another 3 minutes. Positive PCR amplifications are then determined by an electrophoresis on 1.2% agarose gel in 0.5×TAE buffer.

Determination of the Transcription of the Genes Expressing Catalase and Glutathione Peroxidase The total cellular RNA of treated or untreated U937 cells is prepared according to Chirgwin et al. 1979 (Chirgwin J. M., 1979, Biochemistry, 18, 5294).

For the reverse transcription and PCR amplification, procedures are carried out as above.

For the RT-PCR, the primers are described in the literature as follows:

transcription of MnSOD RNA: Beck, Y., 1987, Nucl. Acid. Res., 15, 9076, transcription of Cu/ZnSOD RNA: Sherman, L., 1995, Proc. Natl. Acad. Sci., USA, 80, 5465, transcription of glutathione peroxidase RNA: Mullenbach, G. T., 1987, Nuc. Acid. Res., 15, 5484, transcription of catalase RNA: Ponte, P., 1984, ibid 12, 1687/Sukenaga, Y., 1987, ibid, 15, 7178/Zeviani, M., 1987, Gene, 55, 205.

Role of the Presence of Anti-heterologous SOD Antibodies in the Immuno-redox Activity of Heterologous SODs To show the effect of heterologous SOD/anti-heterologous SOD antibody synergy, the in vitro effects of HSD1/anti-HSD1 antibody immune complexes in the heterologous activity of the SODs were studied.

U937 cells which are chronically infected with HIV-1 (U1 cells), and which have a low p24 production level (<250 pg/10$^5$ cells/ml in a 3-day supernatant) are cultured in an RPMI medium supplemented with L-glutamine, penicillin, streptomycin and foetal calf serum at 10% (Gibco products). They are used for the production of p24, and to evaluate apoptosis.

The anti-HSD1 antibodies are mouse IgG1s (Valbiotech).

Figure 17:
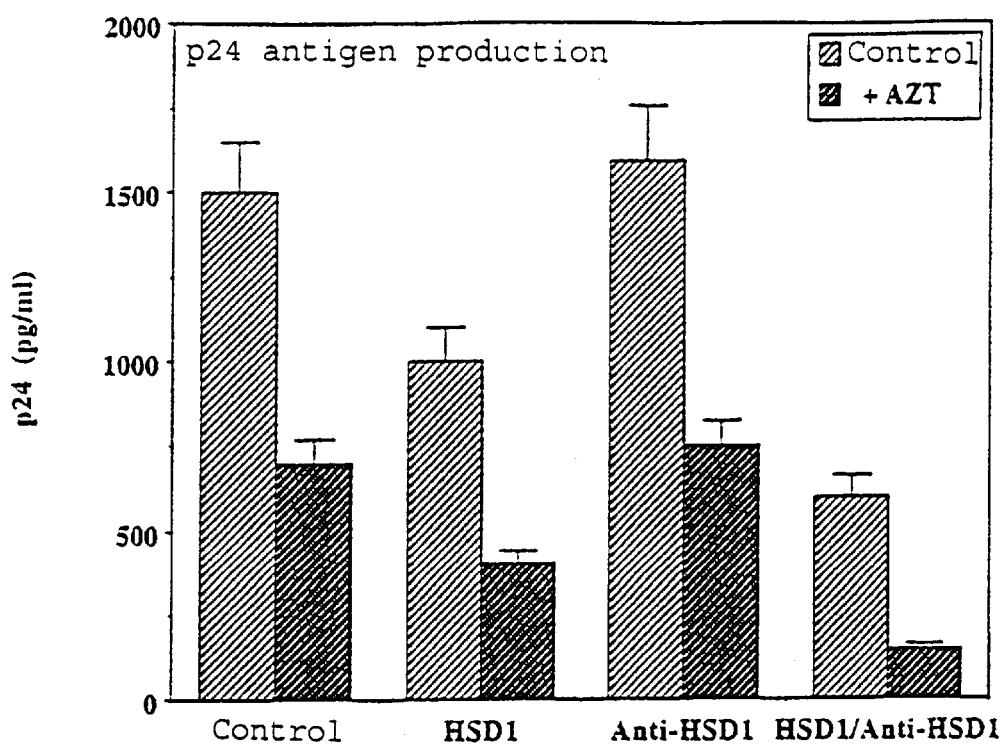
FIGS. 17 and 18 illustrate the effects of anti-HSD1 antibodies combined with an HSD1 on the replication of the HIV-1 virus and the death by apoptosis of U1 cells chronically infected with the virus.
Figure 18:
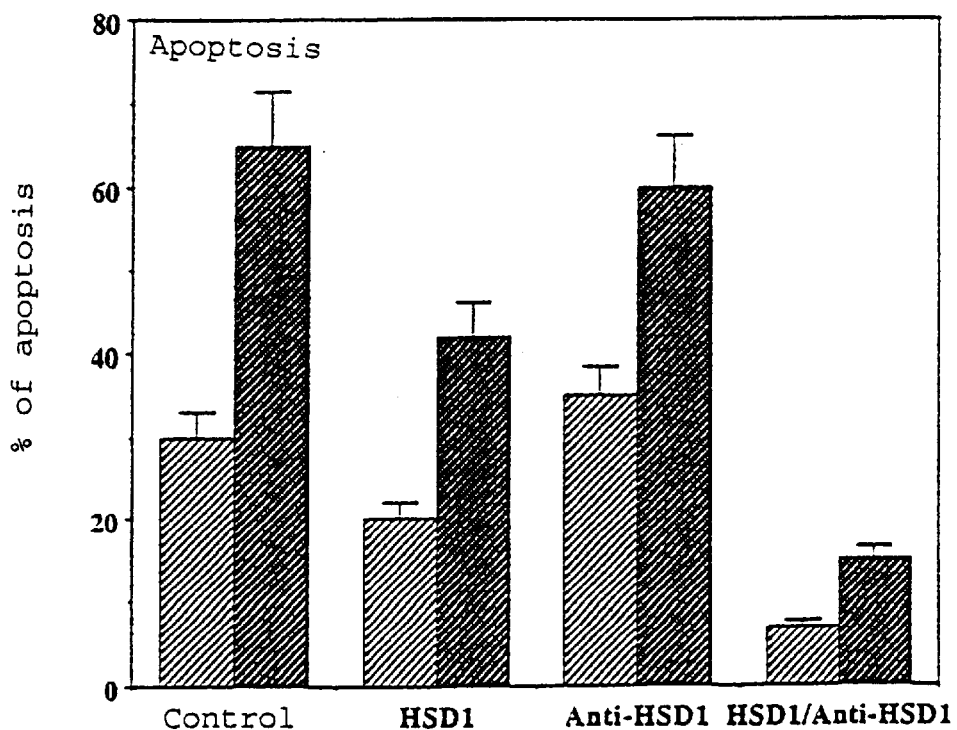

In the experiments carried out (FIGS. 16 to 18), the HSD1 is used at 10 µg/ml, i.e. 30 U/ml, and the anti-HSD1 antibodies are also used at the concentration of 10 µg/ml.

II. Results

Determination of Immuno-redox Activity on the Oxogonous SOD on U937 HIV-Tat Stimulated Cells Endogenous SOD Expression:

The HIV-Tat protein is capable, all by itself, of greatly reducing the expression of the Mn—SOD protein in U937 cells, without changing that of Cu/Zn—SOD (Flores C.S., 1993, Proc. Natl. Acad. Sci. USA, 90, 7632). On the contrary, HSD2 (modified or nonmodified plant SOD), alone, is capable of potentiating the basic expression demonstrated in the nonstimulated U937 cells. The most significant result is obtained for the HIV-Tat activated cells, in which Mn—SOD expression remains undetectable after treatment with human SOD, whereas it is restored after treatment with HSD2, which is a heterologous form with SOD (FIG. 1).

Endogenous SOD Activity

Figure 2:
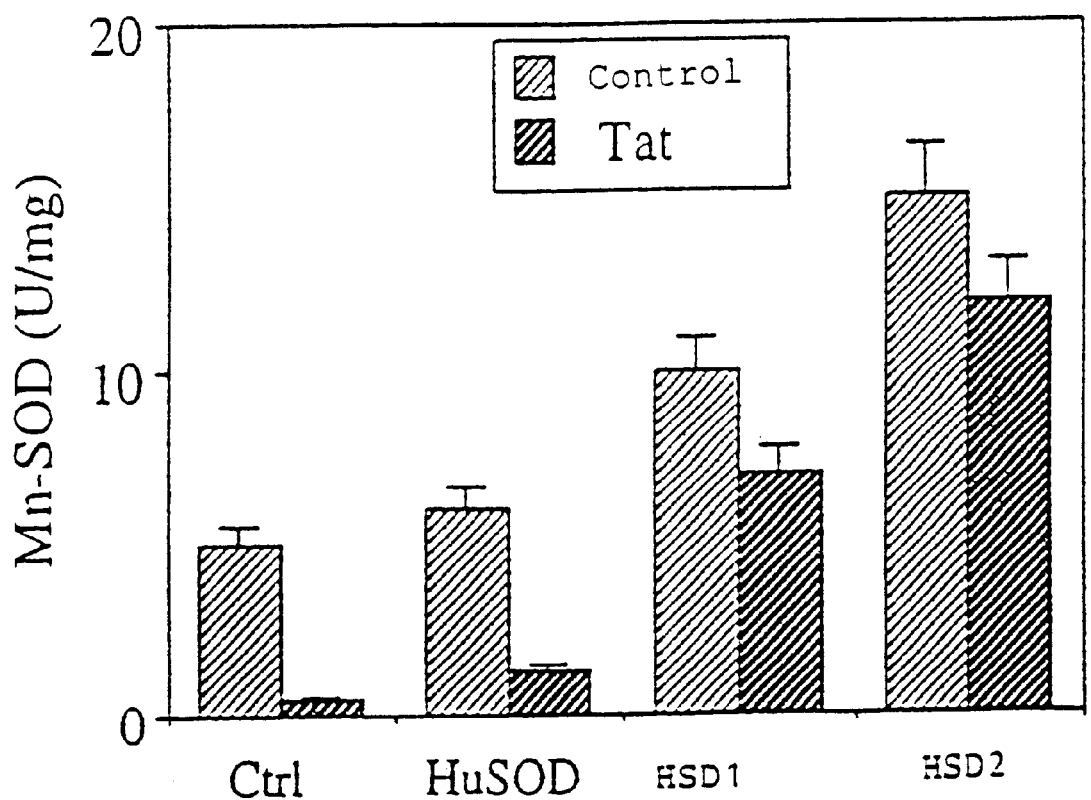
FIG. 2 illustrates the endogenous SOD activity of U937 cells (human promonocytic leukaemia cell line) after activation with an exogenous SOD.

The HIV-Tat protein-induced inhibition of Mn—SOD expression in U927 cells can be lifted by various heterologous SODs: HSD1 (bovine SOD) or HSD2 (plant SOD), whereas it is not lifted by homologous SOD such as human SOD (HuSOD). This suggests that the HIV-Tat protein-induced inhibition of Mn—SOD expression of U937 cells can be lifted by an exogenous SOD only in a heterologous context, as is illustrated in FIG. 2; the Mn—SOD expressed in this context is active.

Endogenous Activation of Other Antioxidant enzymes:

The HIV-Tat protein decreases the total amount of glutathione GSH, which is a substrate in the reduction of peroxides, which is catalysed by glutathione peroxidase (Gpx) in HeLa cells and in Jurkat cells (Westerndorp M.O., 1995, EMBO J.; 14, 546).

Figure 3:
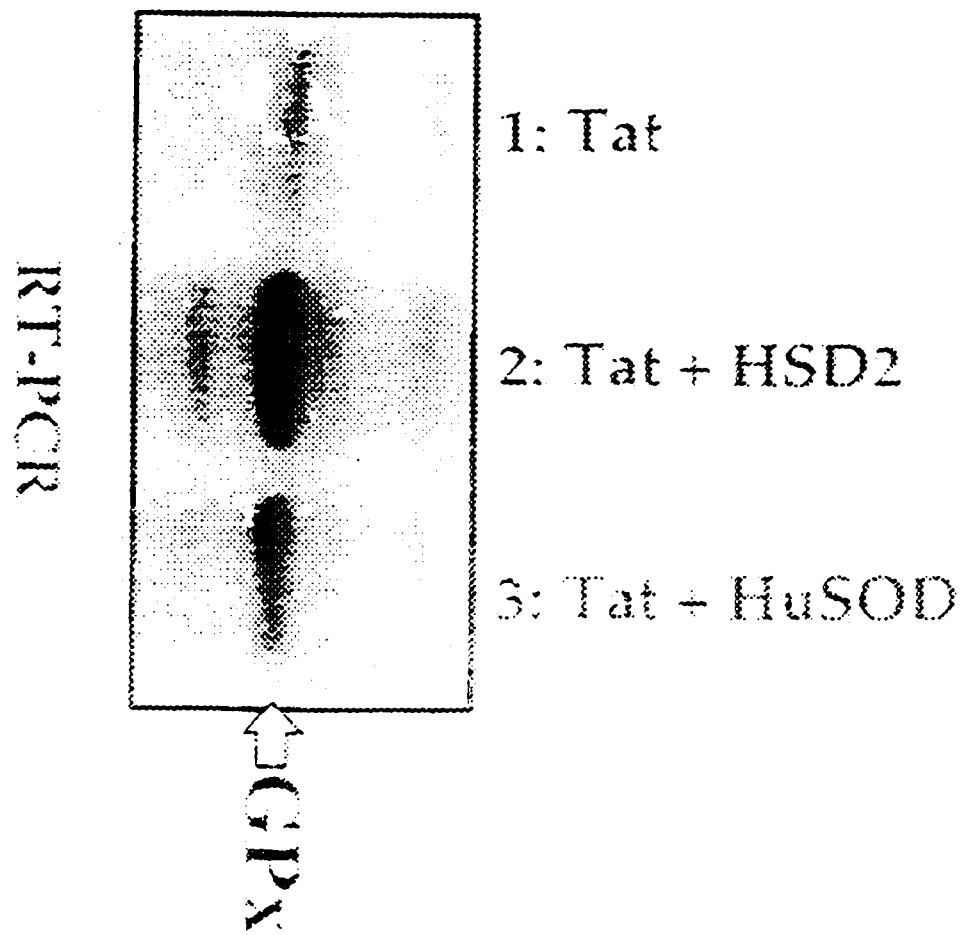
FIG. 3 illustrates the conditions under which an endogenous antioxidant enzyme (glutathione peroxidase) is activated with an exogenous SOD.

While the HIV-Tat protein does not decrease Gpx transcription in U937 cells, plant SOD (HSD2) is capable of stimulating its transcription, whereas HuSOD does not enable it, as is illustrated in FIG. 3.

Figure 4:
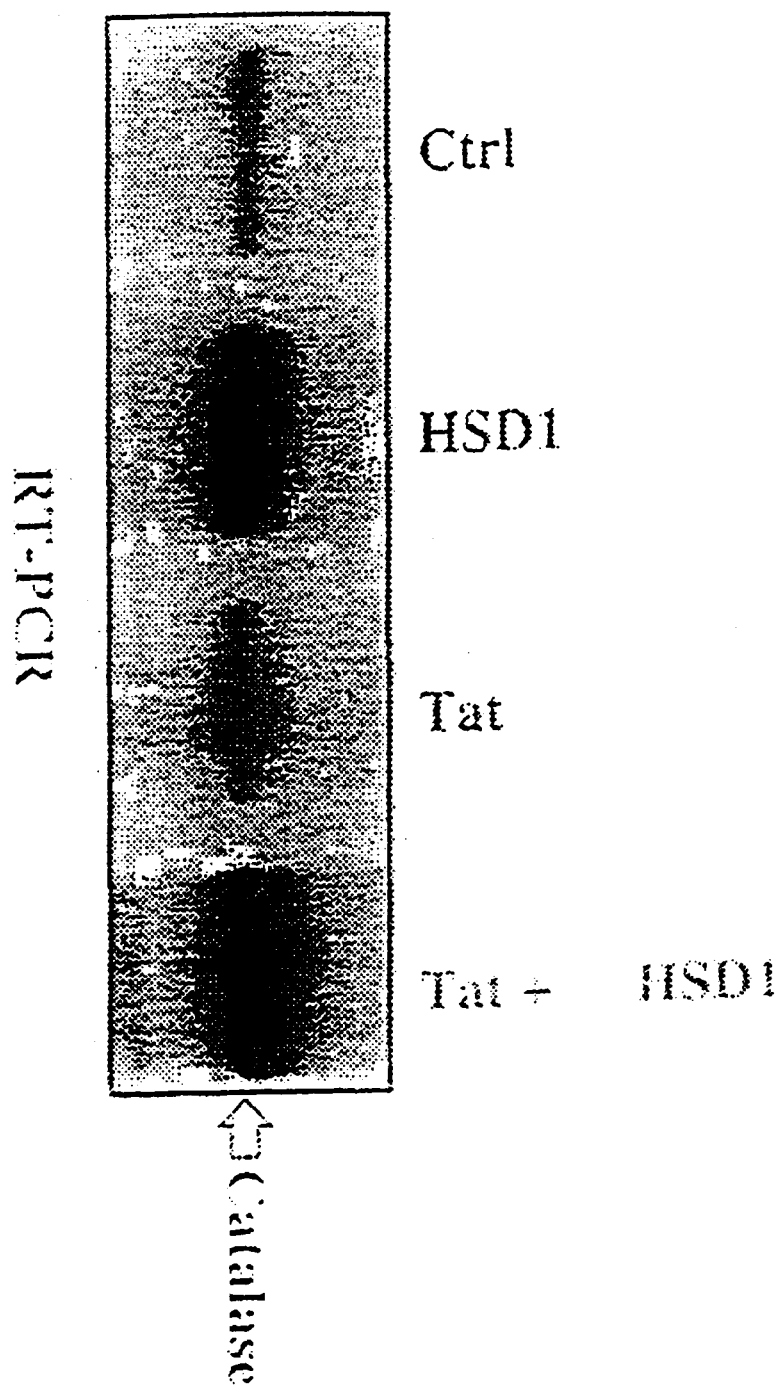
FIG. 4 illustrates the conditions under which an endogenous antioxidant enzyme (catalase) is activated with an exogenous SOD

The same appearance of a potentiation by the heterologous SOD of the level of endogenous catalase transcription can be observed in untreated cells as much as in cells treated with the HIV-Tat protein, as is illustrated in FIG. 4.

These results show that during an oxidative stress such as that observed in the U937 promonocytic cell line during an HIV infection stimulation obtained with the HIV-Tat protein, the overall antioxidant defences, and in particular the lifting of the inhibition of endogenous Mn—SOD, can be restored by a treatment with a heterologous SOD, which is preferably modified, in such a way as to conserve only its immuno-redox activity, whereas they are relatively unmodified by a treatment with homologous SOD.

Effects of HSD1/anti-HSD1 Antibody Immune Complexes in the Immuno-redox Activity of Heterologous SODs.

Figure 16:
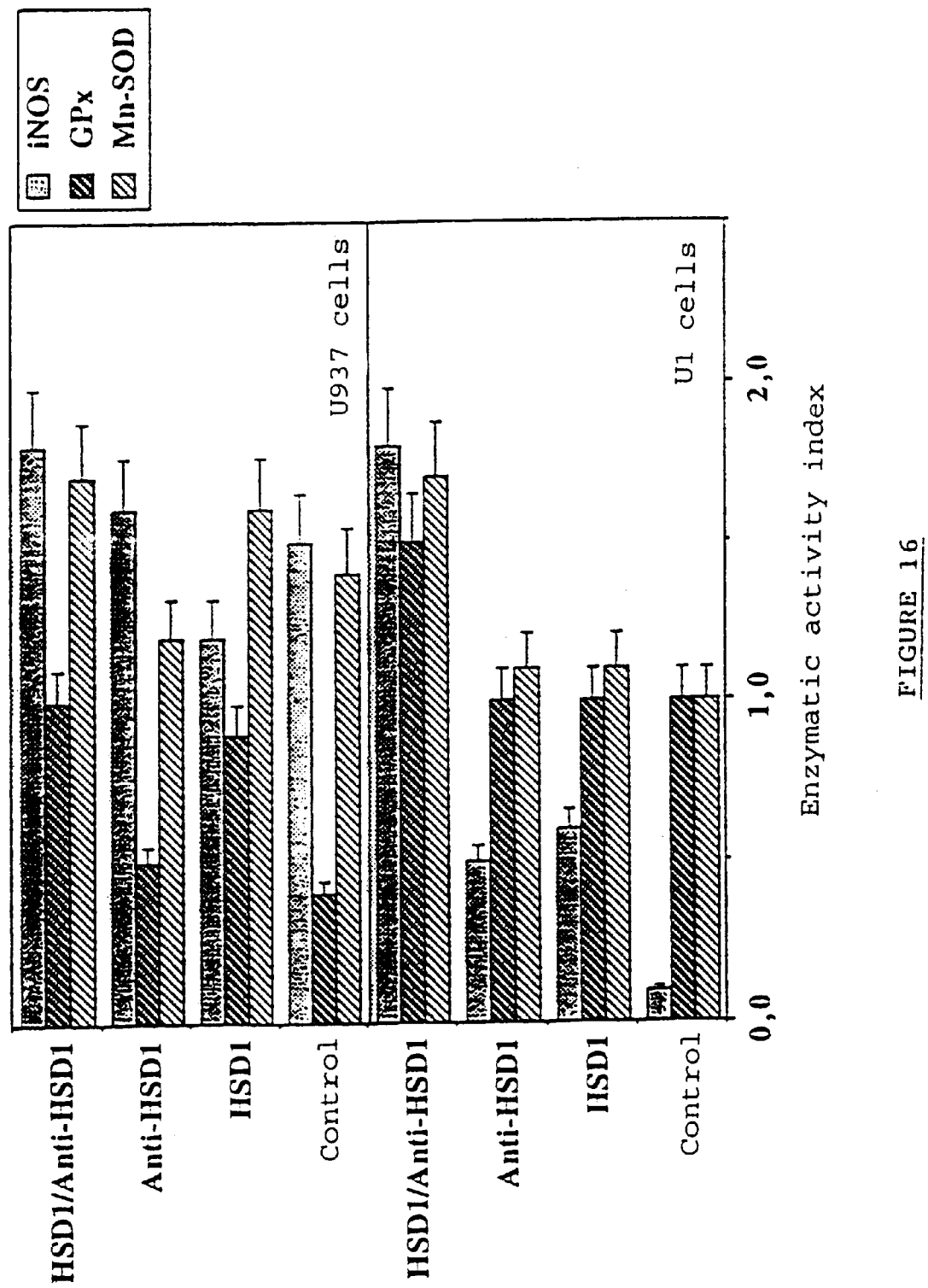
FIG. 16 illustrates the effects of the presence of anti-HSD1 antibodies on the immuno-redox activity of HSD1.

When noninfected U937 macrophage cells and U1 cells chronically infected with HIV-1 are stimulated with the HSD1/anti-HSD1 immune complex, the results illustrated in FIG. 16 are obtained: It is observed that while HSD1s stimulate the expression of glutathione peroxidase (GPx), of Mn—SOD and of inducible NO synthase (iNOs), this stimulation is significantly increased when HSD1 is complexed with an anti-HSD1 antibody. In addition, this same immune complex significantly reduces the replication of the virus HIV-1 (p24 production) by U1 cells stimulated with 10 ng/ml of TNF, and reinforces the effects of a suboptimal dose of AZT (1 μg/ml) (FIG. 17); in the same way, this complex reduces the death by apoptosis of U1 cells stimulated with 10 ng/ml of TNF, in the presence or absence of AZT (FIG. 18) (see also Example 3).

These results show that the HSD1/anti-HSD1 immune complexes significantly reinforce the pharmacological effects of HSD1s. Thus, an optimal pharmacological effect may be obtained with heterologous SODs, since the stimulation of the immune system, after injection or ingestion, induces a supporting immunological activity (production of anti-HSD1 antibodies).

EXAMPLE 2

Demonstration of the Loss of the Dismutase Activity of a Modified SOD (Nitrated SOD)

I. Materials and Methods

Measurement of glutathione peroxidase activity: see Example 1.

Measurement of Mn—SOD: see Example 1.

Target cells: circulating lymphoid cells, or CLC, which are cultured under the same conditions as those set out in Example 1 for U937 cells.

Preparation of nitrated SOD: it is prepared in accordance with the method described in the article in the name of L. A. MacMillan-Crow, which appeared in Proc. Natl. Acad. Sci. USA, 1996, 93, 11853–11858.

II. Results

Figure 5:
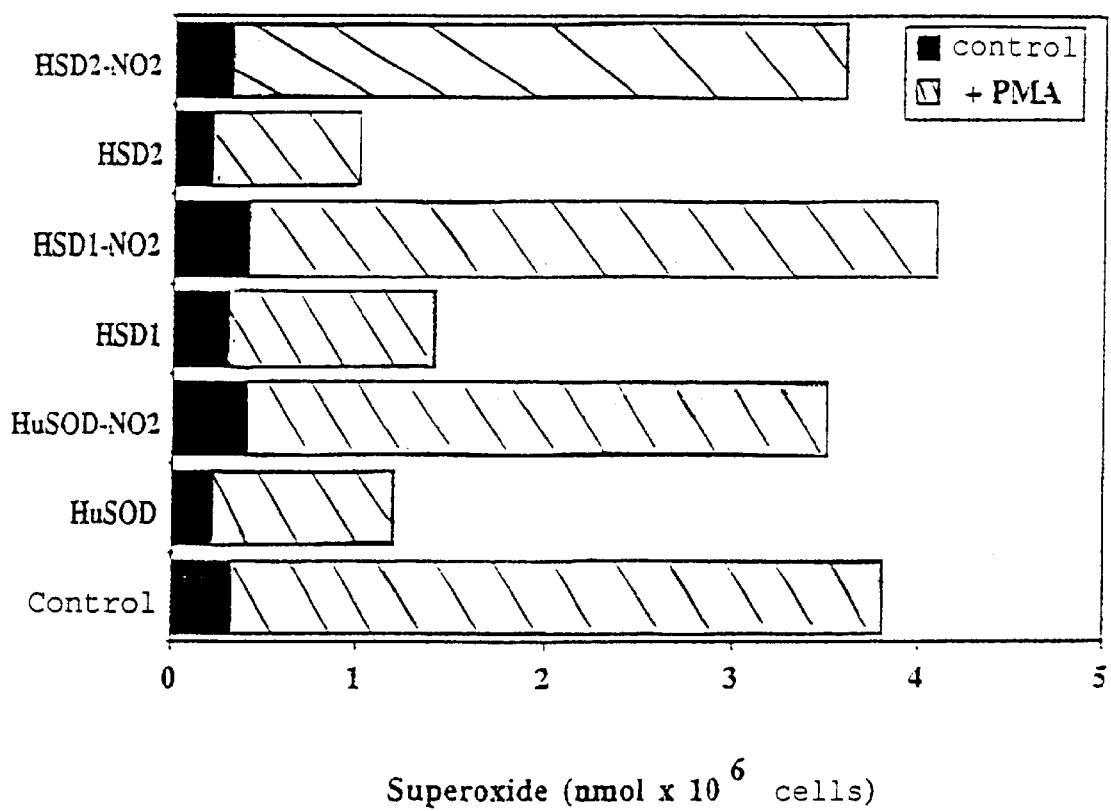
FIG. 5 illustrates the dismutase activity of recombinant human SOD (HuSOD), bovine SOD (HSD1) and plant SOD (HSD2) compared to the dismutase activity of nitrated recombinant human SOD (HuSOD-NO$_2$), nitrated bovine SOD (HSD1-NO$_2$) and nitrated plant SOD (HSD2-NO$_2$)
Figure 6:
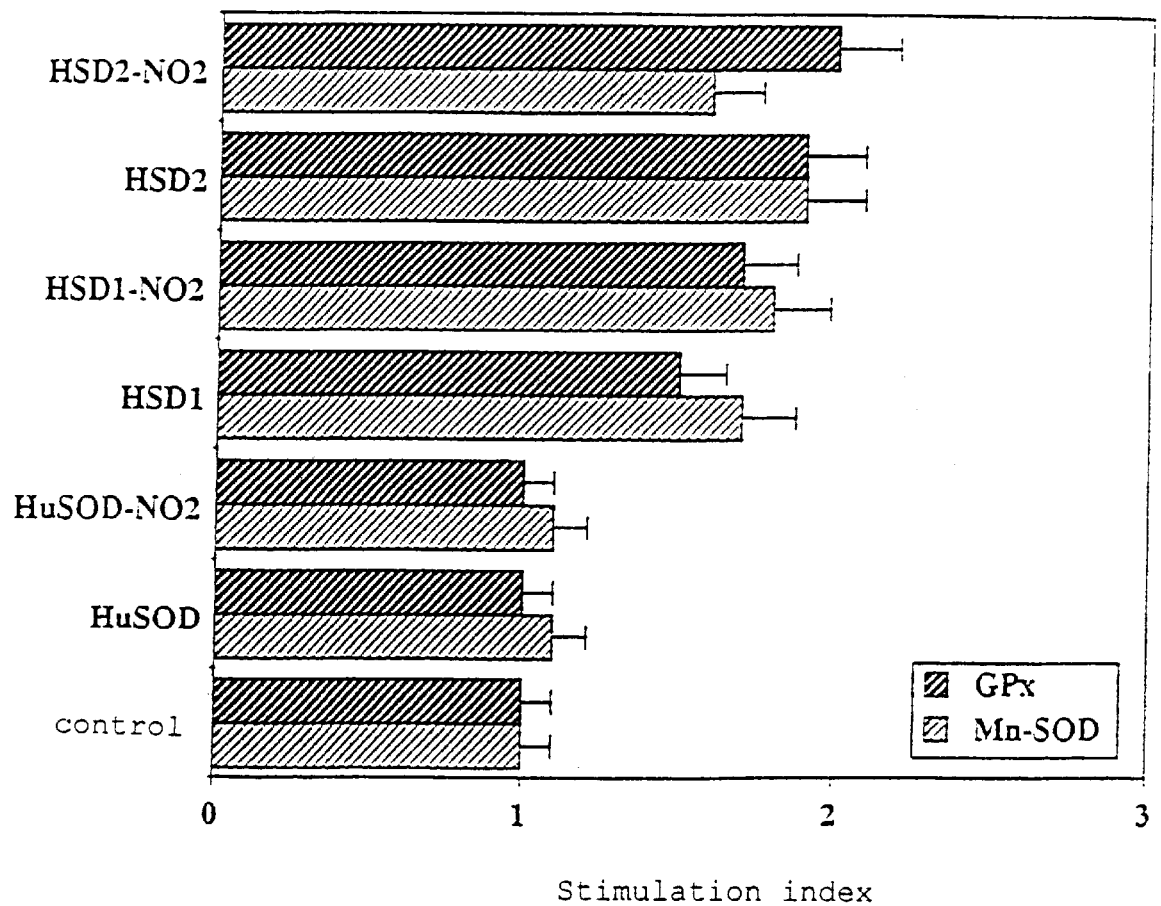
FIGS. 6 and 7 illustrate the compared immuno-redox activity of various SODs.
Figure 7:
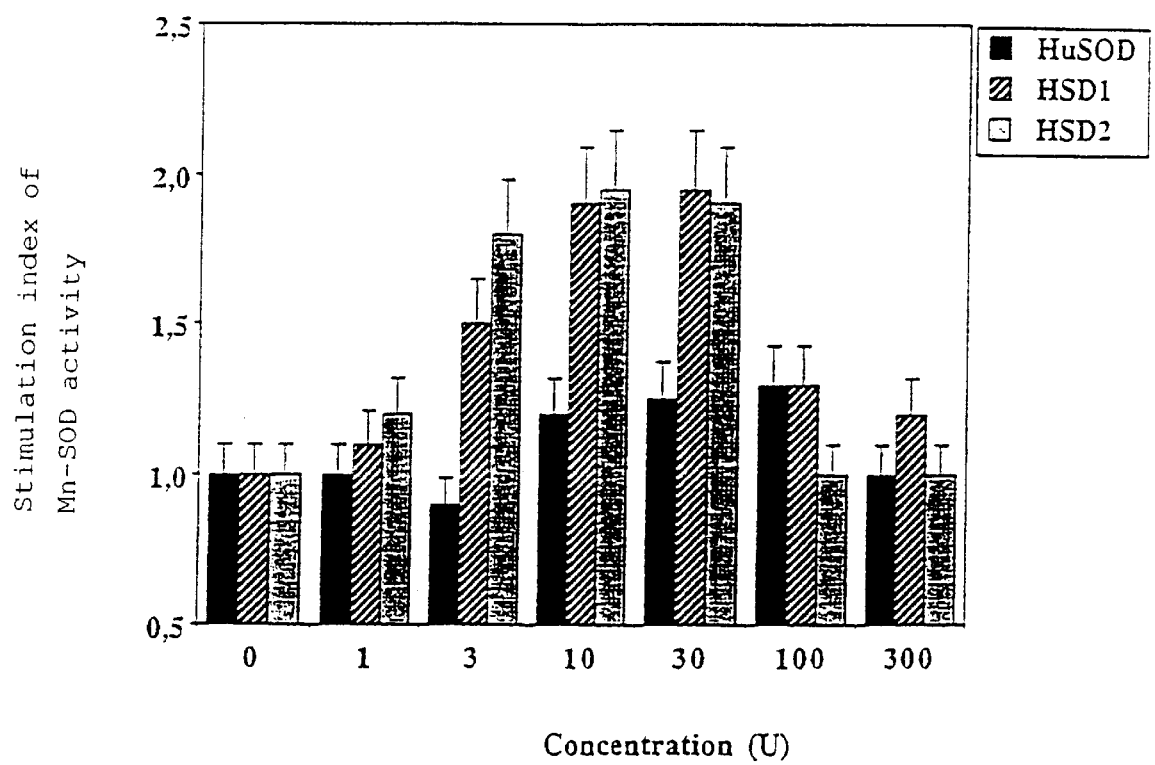

FIG. 5 shows that the nitrated SODs have lost the dismutase activity; specifically, the administration of SOD with essentially immuno-redox activity has no action on the phorbol ester (PMA)-induced production of superoxide anions in circulating lymphoid cells, or CLCs, whereas a stimulation of endogenous glutathione peroxidase and Mn—SOD is observed (FIG. 6 and FIG. 7) in the same target cells.

EXAMPLE 3

Effects of SODs on a Cell Degeneration of Iatrogenic Origin; in the Case of Antiviral Agents I. Materials and Methods Reagents U937 cells which are chronically infected with HIV-1 (U1 cells), and which have a low p24 production level (<250 pg/$10^5$ cells/ml in a 3-day supernatant) are cultured in an RPMI medium supplemented with L-glutamine, penicillin, streptomycin and foetal calf serum at 10% (Gibco products). They are used for the production of p24, and to evaluate apoptosis. The culture medium, the chemical products and the foetal calf serum are tested for their absence of direct effect on these U1 cells (expression of TNF-α and of p24, as activation markers). The cultures are also supplemented with: TSST-1 (staphylococcus exotoxin) (Sigma, Paris, France), human Cu/Zn SOD (HuSOD), bovine SOD (HSD1) (Sigma, St. Louis, Mo.) or melon Cu/Zn SOD (HSD2), supplied by the company Bio-Extraction (Bron, France).

These U1 cells are stimulated with TSST-1 (10 μg/ml), Zinovudine (AZT) (Wellcome) (1 to 10 μg/ml), Saquinavir (Roche) or Ritonavir (Abbott) (10 μg/ml), for 48 hours.

In the control experiments, the antiretroviral products are tested alone.

Some cultures are also supplemented with HuSOD, HSD1 or HSD2, at a final concentration of 30 U/ml.

A preliminary analysis using various concentrations of these reagents made it possible to define these optimum doses.

After 1 to 3 days of incubation, the cell supernatants are recovered, and the levels of p24, of nitrites and of TNF-α are determined.

The viable cells are counted by Trypan blue exclusion.

The HIV-p24 (Pasteur Institute) and TNF-α (Genzyme) proteins are measured by ELISA, according to the manufacturer's recommendations.

NO and $NO_2^-$ are measured by the Greiss reaction.

II. Tests

CLC Cultures for Evaluating TSST-1 and HSD

Isolation and Culture of Human Peripheral Blood Mononucleated Cells (CLCs), which are used to Evaluate the Production of Nitrites and TNF-α, and Apoptosis.

The CLCs are isolated from 10 individuals by centrifugation at 900 rpm for 10 min. to remove the majority of contaminating platelets. The blood samples are then diluted in an RPMI 1640 medium (Bioproduct), and the CLCs are recovered after a 20-min centrifugation at 2000 rpm on a Ficoll-Hypaque gradient (Pharmacia).

These donors exhibit no infection (hepatitis or AIDS) or cirrhosis; some of the donors express rhinitis or an asthmatic state, but were tested outside pollination periods, and in the absence of any treatment.

The CLCs are cultured at a final cell concentration of $2 \times 10^6$ cells/ml in plastic culture plates comprising 12 or 24 wells (Nunc) and in an Iscove medium supplemented with 100 U/ml of penicillin, 100 μg/ml of streptomycin, 1.8 μg/ml of ethanolamine, 40 μg/ml of transferrin, 5 μg/ml of insulin, 2 μg/ml of linoleic acid, 2 μg/ml of oleic acid, 2 μg/ml of palmitic acid, 0.25% of bovine serum albumin and 5% of foetal calf serum.

This culture medium contains no endotoxin (estimation with a limulus test).

The cells are incubated at 37° C. in a humid atmosphere (100%) comprising 95% air and 5% $CO_2$, for 2 to 6 days, in the presence or absence of TSST-1 (10 μM) and of HuSOD, HSD1 or HSD2 (30 U/ml).

Similar experiments are carried out to evaluate the potential toxicological effect of AZT, of Saquinavir or of Ritonavir (10 μg/ml) and the protective effect of the SODs (HuSOD, HSD1 and HSD2 at 30 U/ml).

Assay of Nitrites ($NO_2^-$).

To evaluate the amount of nitric oxide produced (NO°), nitrites ($NO_2^-$), which are a stable final product obtained from nitric oxide, are assayed in the culture supernatants by the Griess reaction. 100 µl of supernatant are added to 96-well microtitration plates, as well as 100 µl of a reactive solution composed of sulphinamide at 1% in acetic acid at 30%, and N-1-naphthylethylenediamine dihydrochloride at 0.1% in acetic acid at 60%.

The standard curve is performed with $NaNO_2$ diluted in Iscove medium. The optical densities (OD) are measured at 540 nm (reader from Dynatech Laboratories Inc., Alexandria, Va.).

Measurement of Apoptosis

The U1 cells or CLC cells which are in early apoptosis are estimated by fluorescence-activated cell sorting (FACS) based on phosphatidylserine in the presence of FITC-labelled annexine V, with or without simultaneous labelling with propidium iodide. The apoptosis-induced DNA fragmentation is also estimated, using the DNA fragmentation detection kit ApoALERT (Clontech, Palo Alto, Calif.).

III. Results

Figure 8:
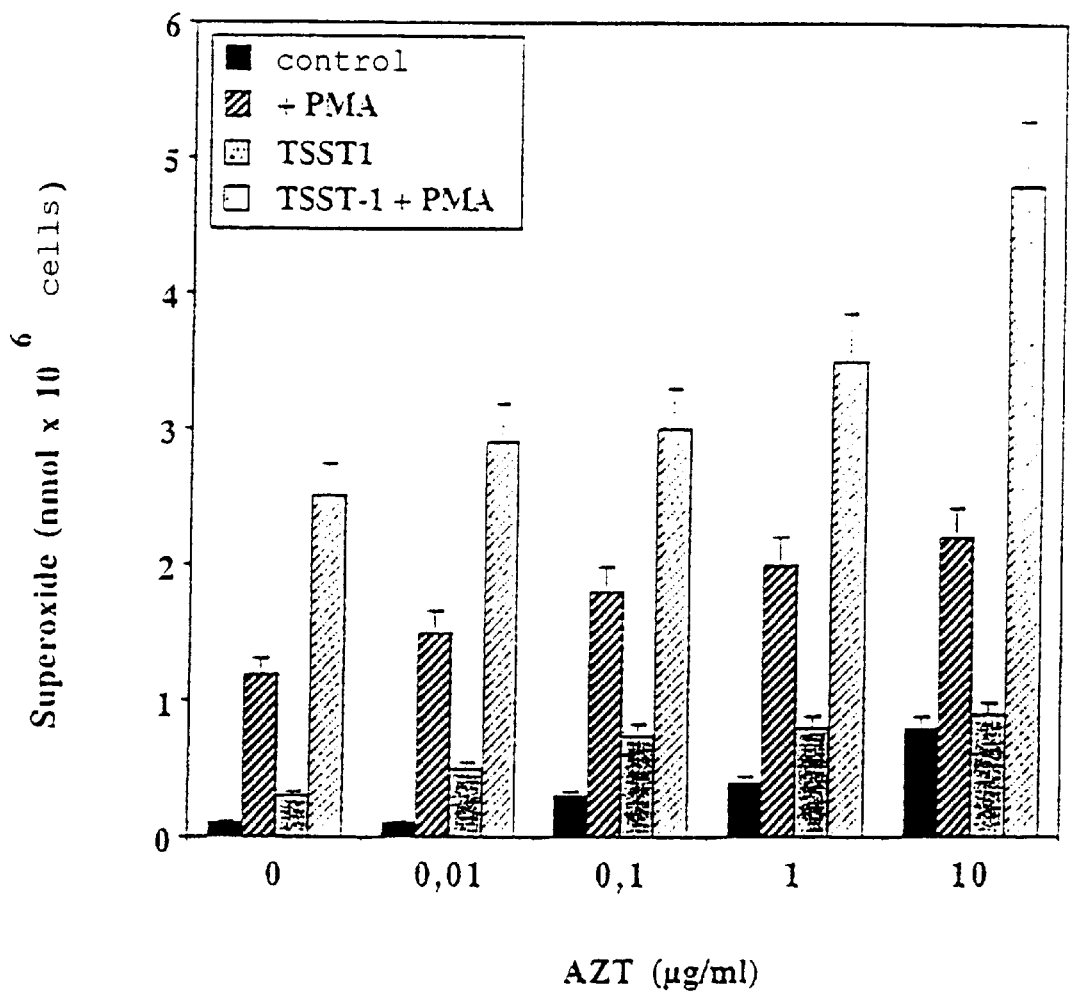
FIGS. 8 and 9A–C illustrate the toxic effect of Zinovudine (AZT) (Wellcome), either spontaneously, or after circulating lymphoid cell (CLC) stimulation with a staphylococcus exotoxin (TSST-1)
Figure 9A:
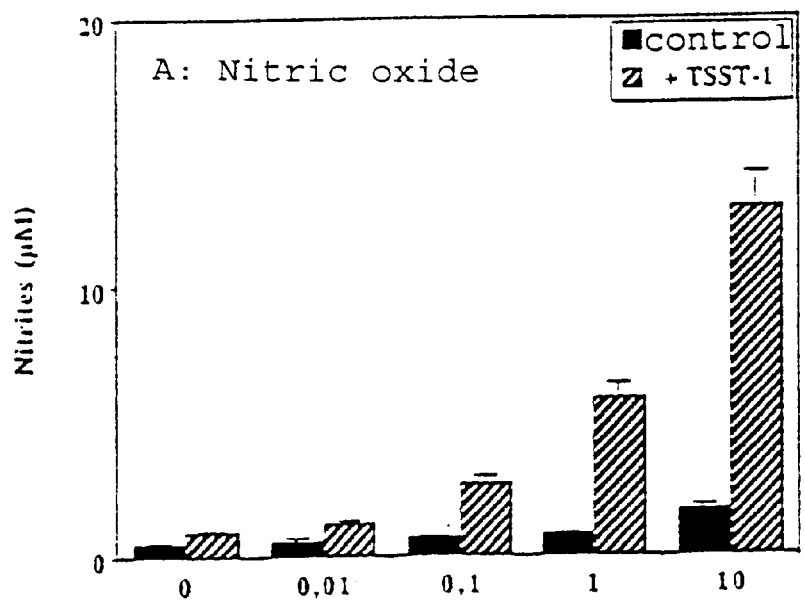
Figure 9B:
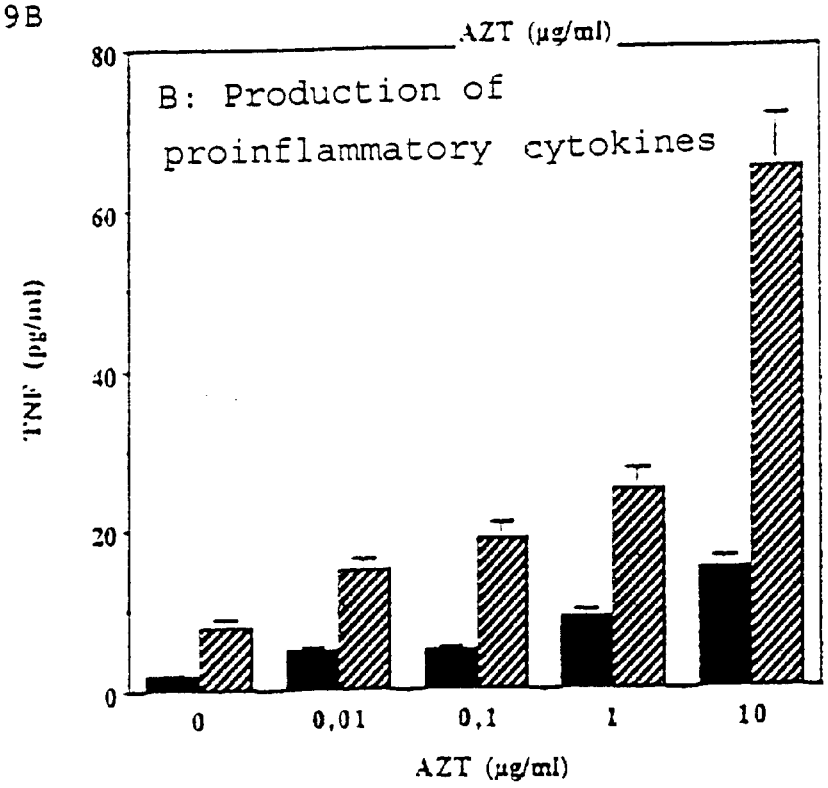
Figure 9C:
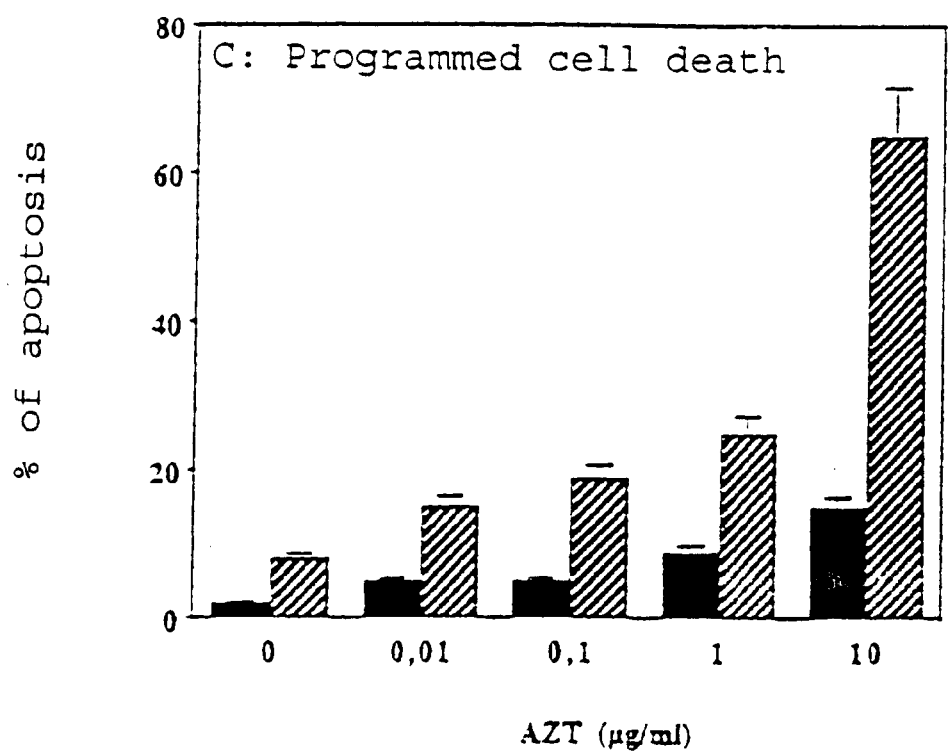
Figure 10A:
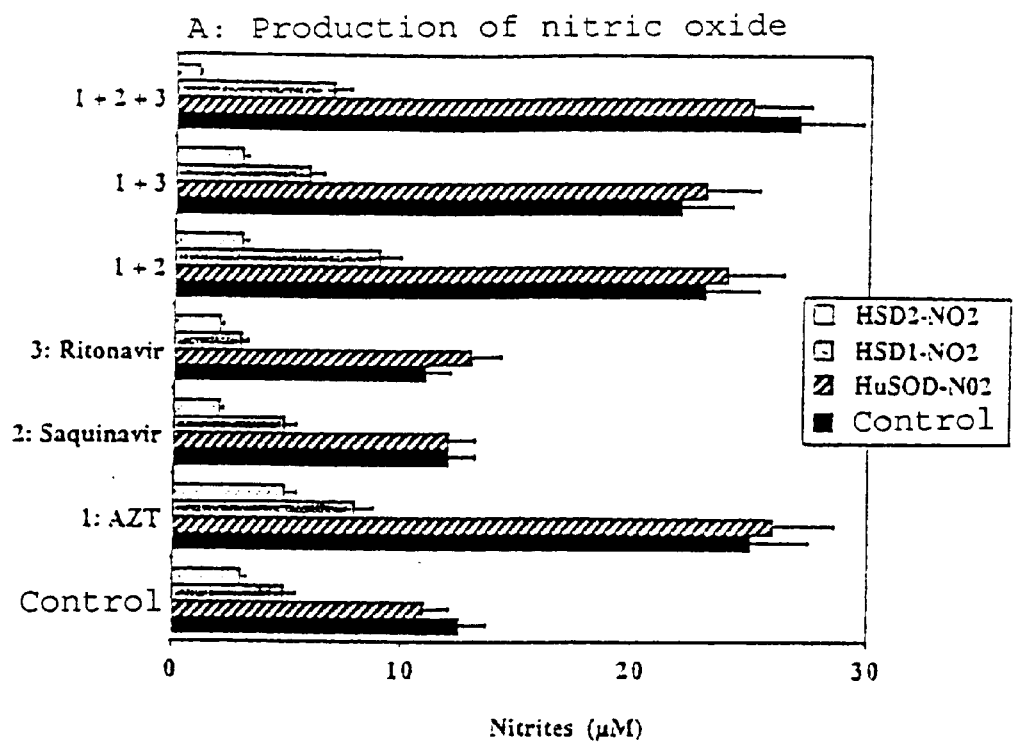
FIG. 10A–C illustrates the toxic effect of several antiretroviral agents on circulating lymphoid cells (CLCs), as well as the effect of nitrated SODs.
Figure 10B:
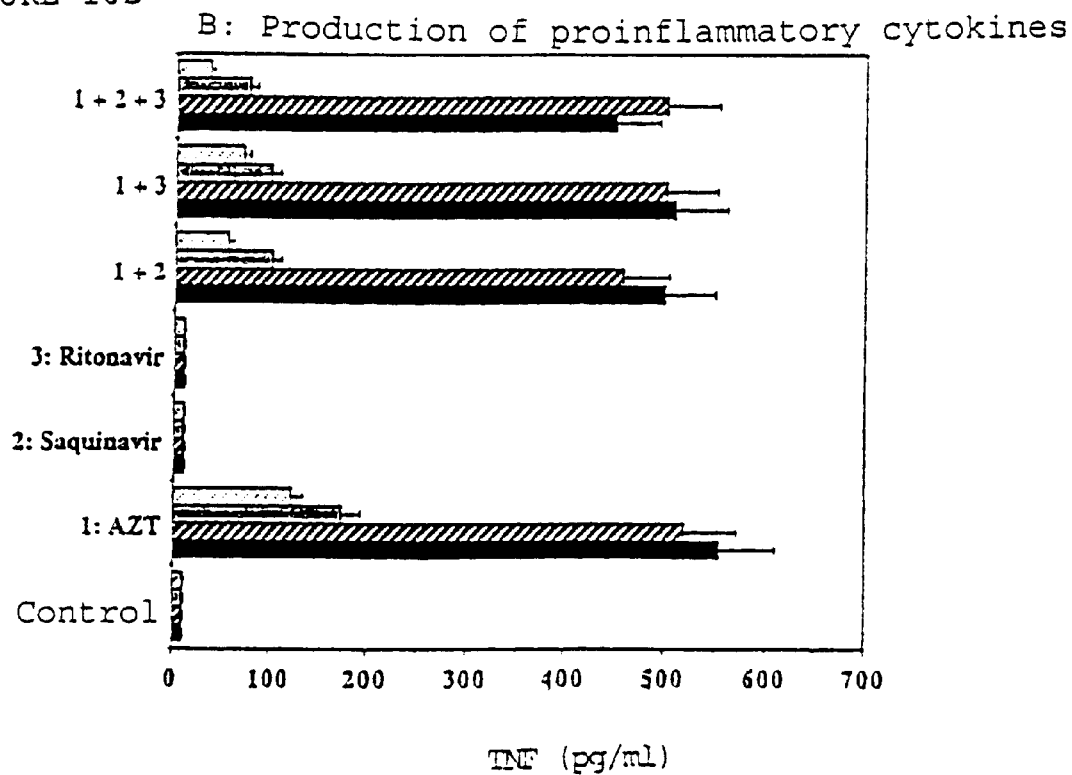
Figure 10C:
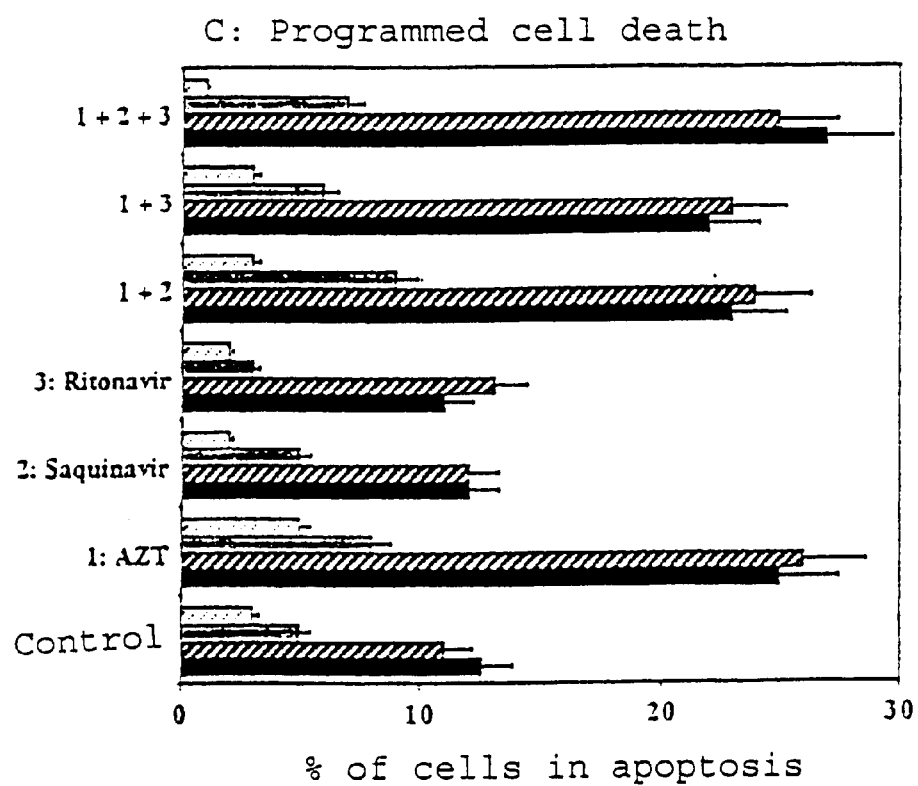
Figure 11A:
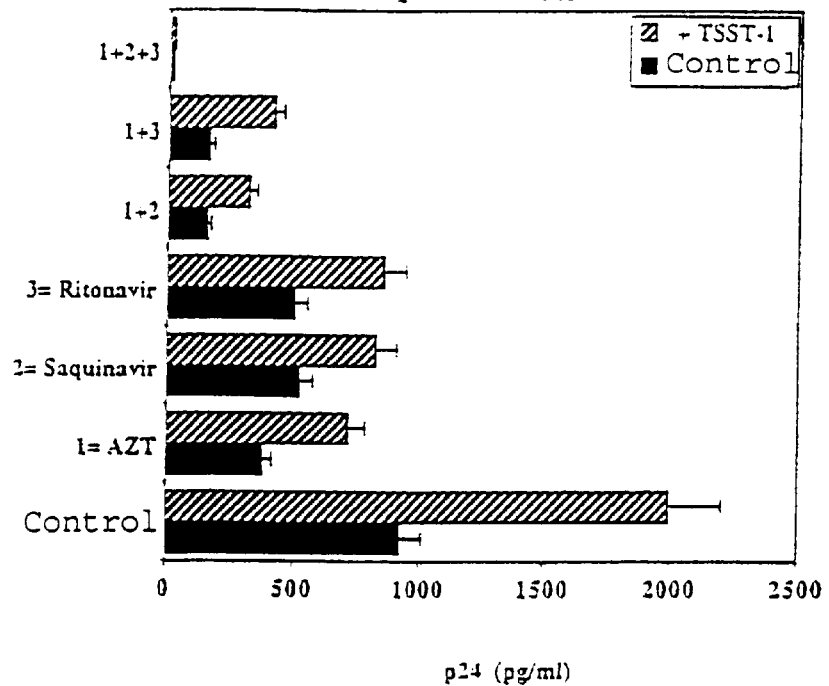
FIG. 11A–B illustrates the effect of AZT on the spontaneous or TSST-1-induced apoptosis of U937 cells which are chronically infected with HIV-1 (U1 cells)
Figure 11B:
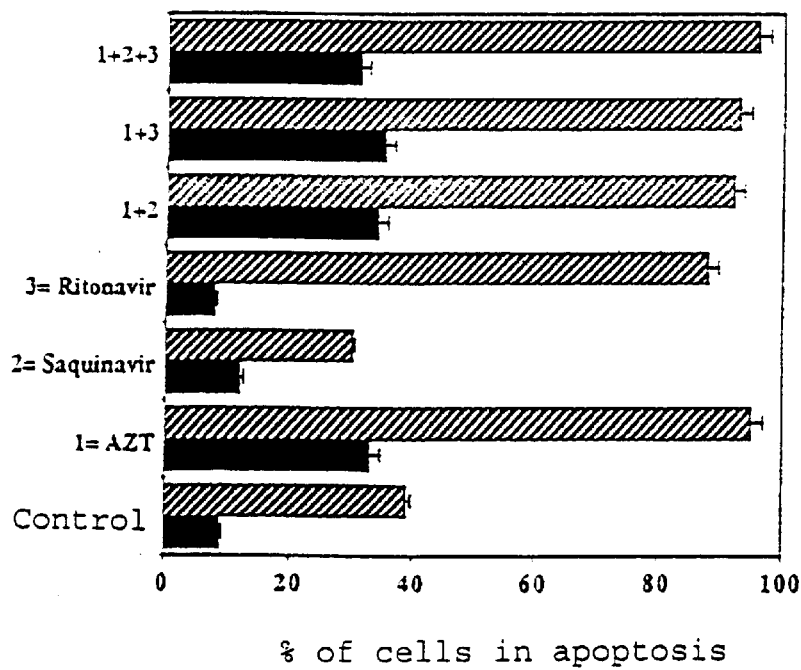

FIGS. 8 and 9 illustrate the toxic effect of AZT (FIG. 8 and FIG. 9), either spontaneously or after the stimulation of the CLCs with staphylococcus exotoxins such as TSST-1; FIG. 10 illustrates the toxic effect of several antiviral agents on the CLCs, as well as the effect of the nitrated SODs; in this FIG. 10, the effect of the nitrated SODs is observed on nitric oxide production (measurement of nitrites (µM)), proinflammatory cytokine production (measurement of TNF (ng/ml)) and the evaluation of cell death (% of cells in apoptosis) in noninfected cells (CLCs) under treatment (monotherapy, bitherapy and tritherapy).

Table I below illustrates the effect of AZT on the viral replication of HIV-1, and on the proinflammatory status of the chronically infected cells (U1).

The results expressed in % of cells in apoptosis (Apoptag Kit) represent the mean SEM of four different experiments.

Effect of the Non-nitrated and Nitrated SODs on the Inflammatory Status of the Cells Infected with HIV-1, Which are Untreated or Treated with an Antiviral Agent.

Table III illustrates the effect of HuSOD, of HSD1 and of HSD2 on viral replication and the programmed cell death of U1 cells chronically infected with HIV-1 (in the presence or absence of antiviral agents).

TABLE III

| Stimulation | p24 (pg/ml) | % of apoptosis |
|---|---|---|
| A: without antiretroviral agent | | |
| Control | 950 ± 25 | 15 ± 2 |
| HuSOD | 700 ± 12 | 10 ± 1 |
| HSD1 | 550 ± 32 | 8 ± 1 |
| HSD2 | 480 ± 23 | 6 ± 2 |
| TSST-1 | 1756 ± 75 | 89 ± 5 |
| TSST-1 + HuSOD | 1290 ± 45 | 75 ± 2 |
| TSST-1 + HSD1 | 900 ± 56 | 30 ± 4 |
| TSST-1 + HSD2 | 923 ± 78 | 34 ± 7 |
| B: in the presence of AZT | | |
| Control | 233 ± 12 | 45 ± 2 |
| HuSOD | 200 ± 27 | 35 ± 1 |
| HSD1 | 125 ± 32 | 18 ± 1 |
| HSD2 | 130 ± 26 | 11 ± 2 |
| TSST-1 | 1056 ± 45 | 98 ± 1 |
| TSST-1 + HuSOD | 890 ± 21 | 70 ± 2 |
| TSST-1 + HSD1 | 300 ± 76 | 17 ± 4 |
| TSST-1 + HSD2 | 223 ± 78 | 15 ± 7 |

TABLE 1

| AZT | Superoxide (+PMA) | | Nitric oxide | | TNF | | p24 antigen | |
|---|---|---|---|---|---|---|---|---|
| (µg/ml) | Control | +TSST-1 | Control | +TSST-1 | Control | +TSST-1 | Control | +TSST-1 |
| 0 | 1.1* | 2.5* | 0.5 | 5.5 | <10 | 275 | 900 | 2512 |
| 0.01 | 1.5 | 3.3 | 0.8 | 6.1 | <10 | 280 | 750 | 2367 |
| 0.1 | 2.3 | 3.5 | 0.9 | 7.0 | <10 | 325 | 620 | 1235 |
| 1 | 2.5 | 4.2 | 0.9 | 12.2 | 55 | 401 | 312 | 809 |
| 10 | 2.9 | 5.1 | 0.9 | 15.3 | 95 | 805 | 100 | 312 |

*The controls without PMA are 0.3 without TSST-1 and from 0.5 with TSST-1
Nitric oxide: the results are expressed in µM nitrites
TNF: the results are expressed in pg/ml
p24 antigen: the results are expressed in pg/ml.

The results are calculated using one series of representative experiments from 5 different ones, and are the mean of quadruplicates, the standard deviation not exceeding 10%.

TABLE II

| | % of cells in apoptosis | |
|---|---|---|
| AZT (µg/ml) | Control | +TSST-1 |
| 0 | 7 ± 2 | 24 ± 3 |
| 0.01 | 9 ± 1 | 27 ± 1 |
| 0.1 | 17 ± 4 | 42 ± 3 |
| 1 | 25 ± 5 | 61 ± 2 |
| 10 | 29 ± 4 | 90 ± 4 |

TABLE III-continued

| Stimulation | p24 (pg/ml) | % of apoptosis |
|---|---|---|
| C: in the presence of Saquinavir | | |
| Control | 763 ± 45 | 15 ± 2 |
| HuSOD | 301 ± 12 | 13 ± 1 |
| HSD1 | 223 ± 33 | 9 ± 1 |
| HSD2 | 170 ± 21 | 10 ± 2 |
| TSST-1 | 925 ± 54 | 75 ± 5 |
| TSST-1 + HuSOD | 700 ± 29 | 65 ± 2 |
| TSST-1 + HSD2 | 208 ± 21 | 19 ± 7 |

TABLE III-continued

| Stimulation | p24 (pg/ml) | % of apoptosis |
|---|---|---|
| D: in the presence of Ritonavir | | |
| Control | 843 ± 56 | 15 ± 2 |
| HuSOD | 658 ± 12 | 10 ± 1 |
| HSD1 | 221 ± 11 | 4 ± 1 |
| HSD2 | 172 ± 19 | 6 ± 2 |
| TSST-1 | 1025 ± 62 | 70 ± 3 |
| TSST-1 + HuSOD | 810 ± 13 | 59 ± 4 |
| TSST-1 + HSD1 | 203 ± 12 | 34 ± 2 |
| TSST-1 + HSD2 | 228 ± 11 | 22 ± 3 |
| E: AZT + Saquinavir + Ritonavir | | |
| Control | 203 ± 13 | 45 ± 2 |
| HuSOD | 150 ± 10 | 30 ± 3 |
| HSD1 | 70 ± 12 | 10 ± 1 |
| HSD2 | 82 ± 14 | 10 ± 2 |
| TSST-1 | 275 ± 24 | 85 ± 3 |
| TSST-1 + HUSOD | 200 ± 21 | 62 ± 3 |
| TSST-1 + HSD1 | 88 ± 10 | 10 ± 2 |
| TSST-1 + HSD2 | 87 ± 11 | 5 ± 1 |

Table IV illustrates the effect of HuSOD, of HSD1 and of HSD2 on the inflammatory status of U1 cells chronically infected with HIV-1.

TABLE IV

| | Nitrites ($\mu$M) | | TNF (pg/ml) | |
|---|---|---|---|---|
| Treatment: | Control | +TSST-1 | Control | +TSST-1 |
| Control | 1 ± 0.5 | 12 ± 3 | <10 | 1256 ± 98 |
| 1: AZT | 5 ± 0.2 | 33 ± 4 | 175 ± 23 | 2934 ± 76 |
| 2: Saquinavir | 1 ± 0.2 | 11 ± 2 | <10 | 1050 ± 72 |
| 3: Ritonavir | 1 ± 0.4 | 10 ± 2 | <10 | 1001 ± 45 |
| 1 + 2 | 1 ± 0.2 | 13 ± 4 | <10 | 1154 ± 87 |
| 1 + 3 | 1 ± 0.1 | 14 ± 2 | <10 | 1212 ± 94 |
| 1 + 2 + 3 | 7 ± 0.4 | 29 ± 3 | 178 ± 21 | 2765 ± 34 |
| 4: HuSOD | 1 ± 0.2 | 9 ± 2 | <10 | 1145 ± 12 |
| 1 + 4 | 4 ± 0.3 | 20 ± 4 | 154 ± 22 | 975 ± 44 |
| 1 + 2 + 3 + 4 | 6 ± 0.2 | 24 ± 5 | 109 ± 17 | 999 ± 65 |
| 5: HSD1 | 1 ± 0.2 | 3 ± 1 | <10 | 221 ± 21 |
| 1 + 5 | 2 ± 0.3 | 9 ± 1 | 55 ± 10 | 175 ± 22 |
| 1 + 2 + 3 + 5 | 1 ± 0.4 | 5 ± 1 | 23 ± 2 | 108 ± 11 |
| 6: HSD2 | 1 ± 0.1 | 4 ± 2 | <10 | 209 ± 45 |
| 1 + 6 | 1 ± 0.2 | 11 ± 4 | 33 ± 2 | 200 ± 14 |
| 1 + 2 + 3 + 6 | 1 ± 0.3 | 6 ± 1 | 25 ± 4 | 109 ± 19 |

Tables III and IV show that under the action of TSST-1 alone or in the presence of antiretroviral agents, a large increase in viral replication and in apoptosis is noted, while the HSDs significantly reduce these effects; conversely, HuSOD has no or few effects.

These results demonstrate that the HSDs reinforce the effects of the antiretroviral agents, while at the same time inhibiting their toxic effects.

EXAMPLE 4

Effects of SODs on a Degenerative Pathology; in the Case of Alzheimer's Disease and Parkinson's Disease I. Materials and Methods Culture for Evaluating the Effects of β-amyloid and MPTP Proteins Isolation of Human Macrophages The CLCs are isolated from 23 healthy individuals, under the same conditions as those set out above. The adherent cell populations are obtained by incubating the CLCs ($1 \times 10^7$ cells/ml) either in Petri dishes (Nunc) or in 6-well culture plates (Nunc) for 30 min at 37° C. in an RPMI 1640 medium supplemented with foetal calf serum at 10% (v/v). The monocytes are then recovered by scraping the plates after adding a cold solution of PBS containing 1 mM EDTA. Cell preparations which comprise more than 85% of viable macrophages are estimated by Trypan blue exclusion and staining with a nonspecific esterase.

Macrophage Culture.

The macrophages are cultured at a final concentration of $2 \times 10^6$ cells/ml in 12- or 24-well plastic culture plates (Nunc) and in an Iscove medium supplemented with 100 U/ml of penicillin, 100 $\mu$g/ml of streptomycin and 5% of foetal calf serum.

This culture medium does not contain any endotoxin. The cells are incubated for 48 hours at 37° C. in a humid atmosphere (100%) containing 95% air and 5% $CO_2$, in the presence of absence of 10 $\mu$g/ml of β-amyloid or MPTP.

The cell supernatants are recovered for measuring the TNF and the nitrites, while apoptosis is evaluated directly on the cells.

II. Results

Figure 12:
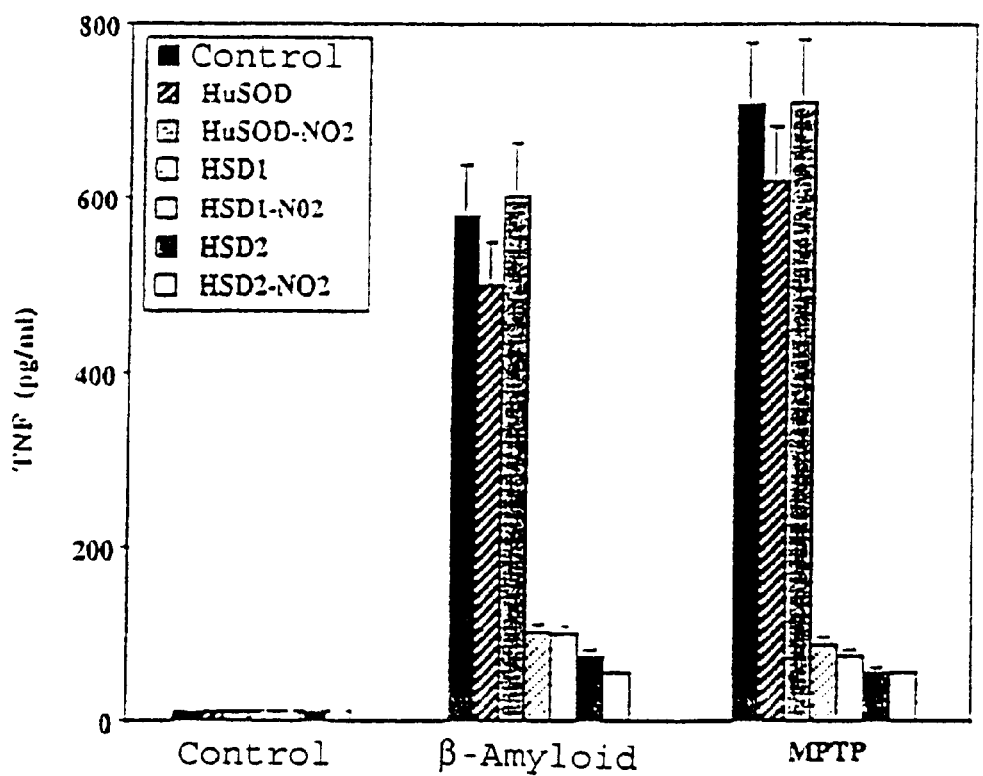
FIGS. 12 and 13 illustrate the in vitro effect of various SODs on cells from two degenerative pathologies, i.e. Alzheimer's and Parkinson's patients.
Figure 13:
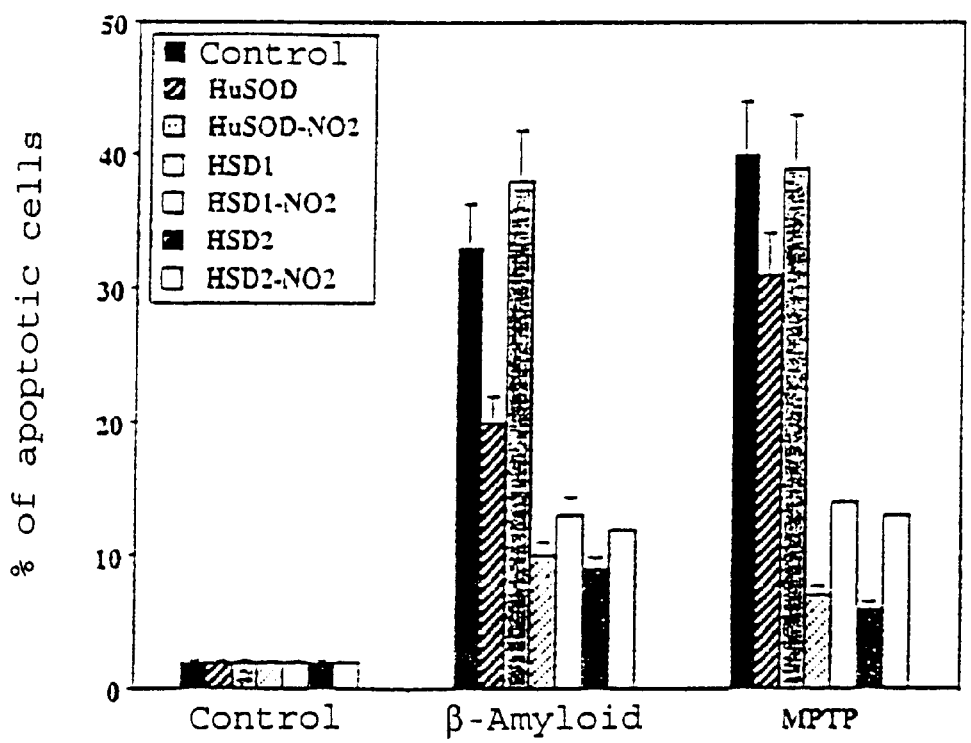

FIGS. 12 and 13 illustrate the results obtained.

These figures show that β-amyloid and MPTP proteins stimulate the production of TNF-α by macrophages and induce their death by apoptosis.

The modified or unmodified HSDs significantly reduce these effects, whereas the HuSOD (modified or unmodified) has no or few effects.

EXAMPLE 5

Effects of SODs on a Degenerative Pathology; in the Case of Radiation-induced Fibrosis The development of fibrosis appears during most chronic hepatopathies of varied origins; infectious or viral (hepatitis), parasitic (bilharzia) or toxic (alcohol, heroin).

Fibrous tissue, when developing, causes an imbalance in the functional unit of the organ and acts on certain cell populations, principally perisinusoidal cells, located in the space of Disse.

The characterization of the effector cells for fibrosis, the regulation of cytokines on matrix deposit, and the standardization of serum and tissue means of controlling the evolution of the disease in humans make it possible to establish therapeutic approaches to limit, reduce or stop any abnormal process of fibrogenesis.

Among the parasitic diseases studied, schistosomiasis is responsible for a chronic hepatic pathology which leads to the formation of a matrix deposit which is at the origin of portal hypertension.

The experimental model of murine hepato-splenic bilharzia caused by *Schistosoma mansoni* makes it possible to show the action of an SOD with immuno-redox activity.

After infection of the mice, the initial lesion is a cell-mediated granulomatous inflammation which develops around the eggs located in the portal radicals, which leads progressively to periovular, and then lobular, fibrosis, subsequent to the activation of heptatic stellate cells (lipocytes), in the space of Disse.

Since fibrosis evolves according to a dynamic process, it can improve following certain antifibrotic treatments; cytokines (α, β and/or γ interferon), corticosteroids or antioxidants (SOD).

The antifibrotic activity of SODs has already been described (PCT International Application WO 96/16670 and Delanian et al., 1992 and Lefaix et al., 1996); however, the risk of a proinflammatory action still exists, whereas the SODs according to the present invention make it possible to avoid such a risk.

I. Materials and Methods

Animals: 90 female OF1 SPF mice of 26/28 g (IFFA-CREDO, Les Oncins, L'Arbresle)

Infestation: each mouse receives, intraperitoneally, 120 cercariae of the Puerto Rico strain of *Schistosoma mansoni*.

Protocol 1:
1. 5 noninfected control mice
2. 5 infected control mice
3. 25 mice which are infested and treated simultaneously for 8 weeks with 3 I.M. injections/week in accordance with the following distribution:
   5 placebo mice: 0.9% NaCl
   10 mice: bovine SOD, 1 mg/kg I.M.,
   10 mice: bovine SOD, 2 mg/kg I.M., Protocol 2:
1. 5 noninfected control mice
2. 5 infected control mice
3. 45 mice which are infested and treated simultaneously for 16 weeks with 3 I.M. injections/week or 3 gavages/week in accordance with the following distribution:
   5 placebo mice: 0.9% NaCl
   10 mice: bovine SOD, 1 mg/kg I.M.,
   10 mice: bovine SOD, 2 mg/kg I.M.,
   10 mice: melon SOD, 2 mg/kg by gavage:
   10 mice: melon SOD, 4 mg/kg by gavage.

Samples:
serum: freezing at $-20°$ C. for the optional study of serum markers liver: a fragment is fixed in AFA (Alcohol, Formol, Acetic Acid) for the histological and morphometric study, and another fragment is frozen for the biochemical assays.

II. Results

Macroscopic analysis of the liver: aspect, distribution of granulomas.

Figure 14:
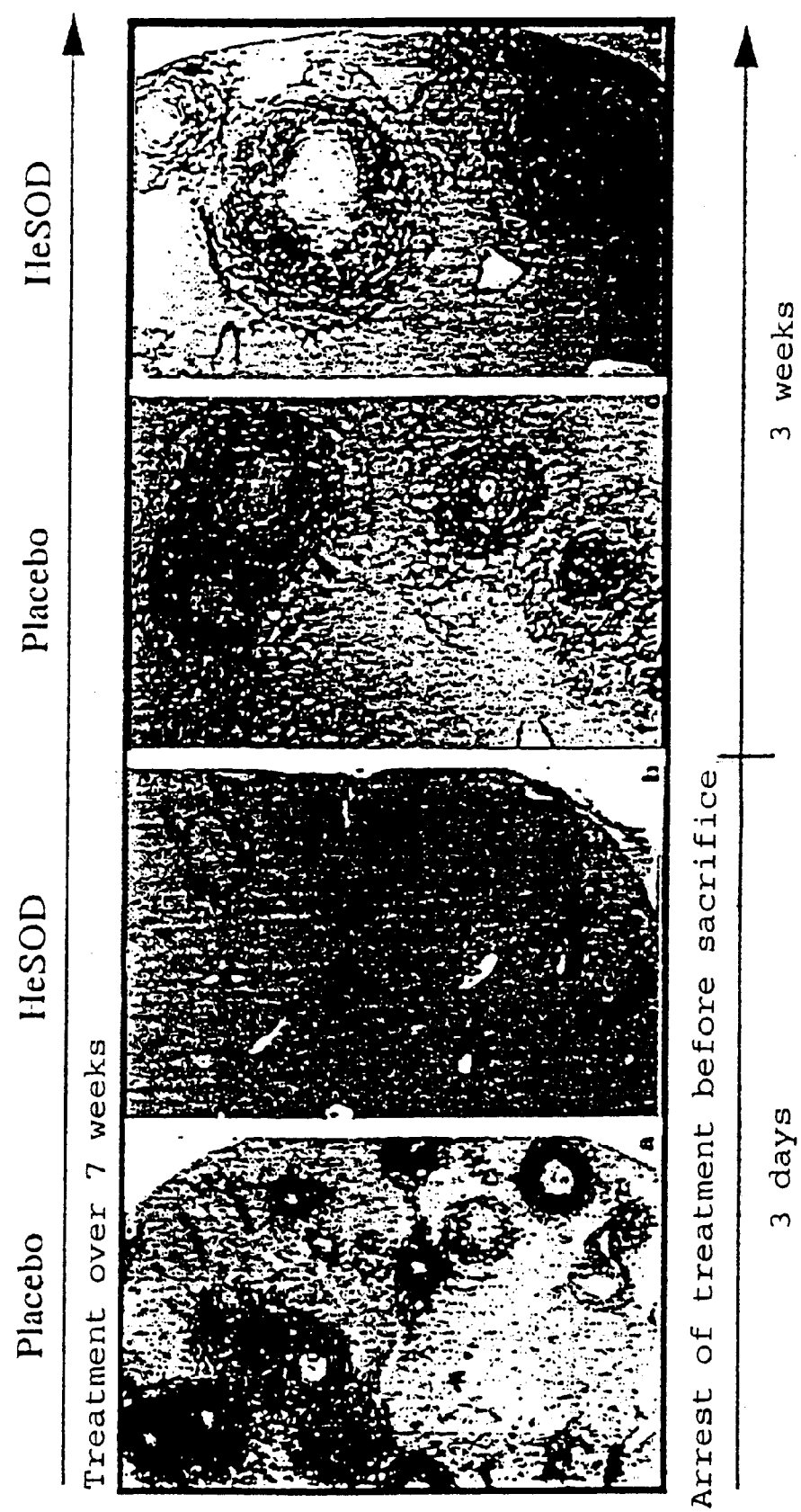
FIGS. 14 and 15A–D show the effects of SODs on a liver degenerative pathology in the case of radiation-induced fibrosis.
Figures 15A, 15B:
Figures 15C, 15D:
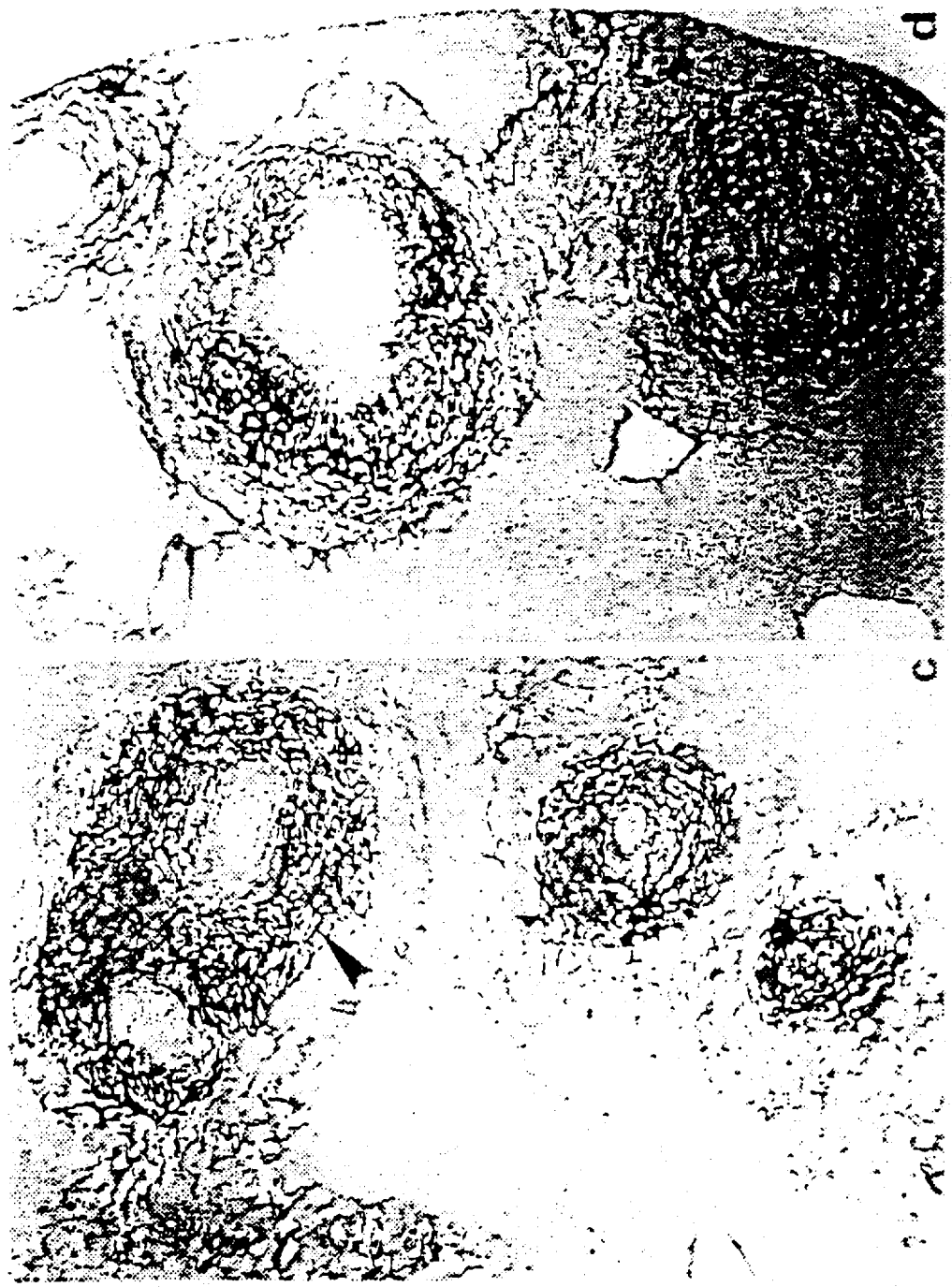

Qualitative histological analysis: descriptive study of the lesions and semi-quantitative evaluation of the inflammation and of the fibrosis on 5-mm histological sections stained with haematoxylin-phloxin-saffron (FIG. 14) and picrosirius red (FIG. 15), respectively.

Quantitative analysis of the fibrous deposits as a whole by colorimetric assay based on the dye affinites of sirius red for collagen and fast green for proteins; the results are expressed in $\mu$g of collagen/mg of proteins.

As emerges from the above, the invention is in no way limited to those of its methods of implementation, preparation and application which have just been described more explicitly; on the contrary, it encompasses all the variants thereof which may occur to persons skilled in the art, without departing from the context or scope of the present invention.

What is claimed is:

1. A treatment method comprising administering to a host in which cell and organ degeneration is observed a medicinal product comprising a plant heterologous superoxide dismutase (SOD) with immuno-redox activity and without a dismutase activity.

2. A method according to claim 1, characterized in that said SOD is nitrated.

3. A method according to claim 1, wherein said SOD is derived from melon.

4. A method according to claim 1, wherein said degenerative disease is selected from the group consisting of neurodegenerative disease, cirrhosis, lentivirus infectons, parasite infections and iatrogenic diseases.

5. A method for selecting a plant SOD with immuno-redox activity useful for treating organ degeneration comprising:
   (a) measuring the dismutase activity of an SOD, or of a modified SOD,
   (b) selecting modified SODs without dismutase activity,
   (c) measuring the immuno-redox activity of the SODs selected in (b) in a cellular system in which expression of endogenous SOD is suppressed, and
   (d) selecting a SOD with immuno-redox activity.

6. A method according to claim 5, wherein step (a) for measuring the dismutase activity is carried out by reduction of ferricytochrome c.

7. A method according to claim 5, wherein the system according to step (c) consists of cells expressing the Tat protein of HIV-1.

8. A method for preparing a medicinal product with immuno-redox activity intended for medicinal detoxification comprising the step of selecting a plant heterologous SOD according to the method of claim 5 as the active ingredient.

* * * * *